United States Patent [19]

Wright

[11] Patent Number: 4,864,849

[45] Date of Patent: Sep. 12, 1989

[54] VISCOMETER

[75] Inventor: Hubert A. Wright, Lexington, Mass.

[73] Assignee: Cambridge Applied Systems, Inc., Cambridge, Mass.

[21] Appl. No.: 203,254

[22] Filed: Jun. 7, 1988

[51] Int. Cl.$^4$ ............................................. G01N 11/12
[52] U.S. Cl. ............................................ 73/57; 73/54
[58] Field of Search ....................................... 73/54, 57

[56] References Cited

U.S. PATENT DOCUMENTS 3,677,070  7/1972  Norcross ................................. 73/57
4,627,272  12/1986  Wright ..................................... 73/57

FOREIGN PATENT DOCUMENTS 0486249  1/1976  U.S.S.R. ................................. 73/57

Primary Examiner—Stewart J. Levy
Assistant Examiner—Michele Simons
Attorney, Agent, or Firm—Nutter, McClennen & Fish

[57] ABSTRACT

A viscometer (10) includes a chamber-defining cylinder (22) within which a bob (26), including a ferromagnetic collar (30), is shuttled back and forth by alternate driving of two coils (32 and 34). Measurement circuitry (FIG. 2) determines the viscosity of fluid inside the chamber (24) by measuring the time required for the bob (26) to make a round trip consisting of one stroke in each direction. By employing round-trip time rather than single-stroke time, the viscometer (10) reduces the sensitivity of the viscosity measurement to orientation with respect to gravity.

10 Claims, 6 Drawing Sheets

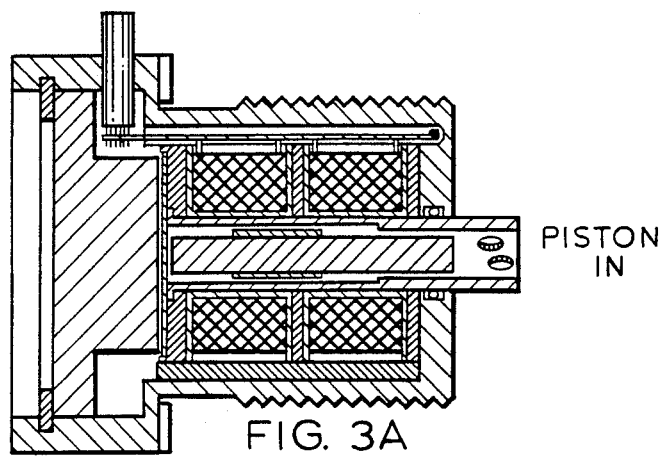
FIG. 3A — PISTON IN
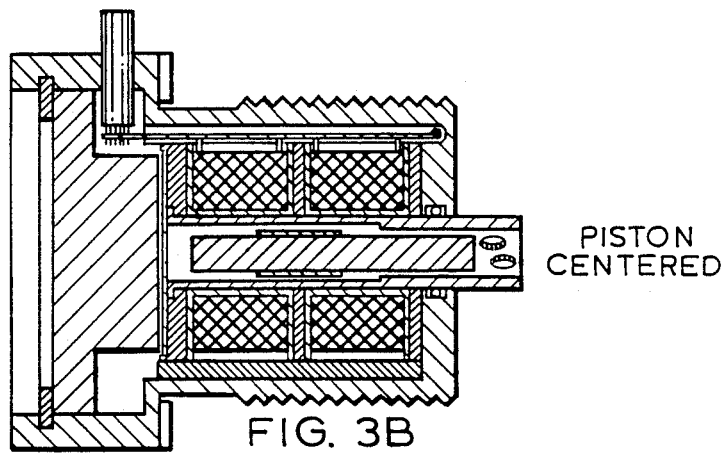
FIG. 3B — PISTON CENTERED
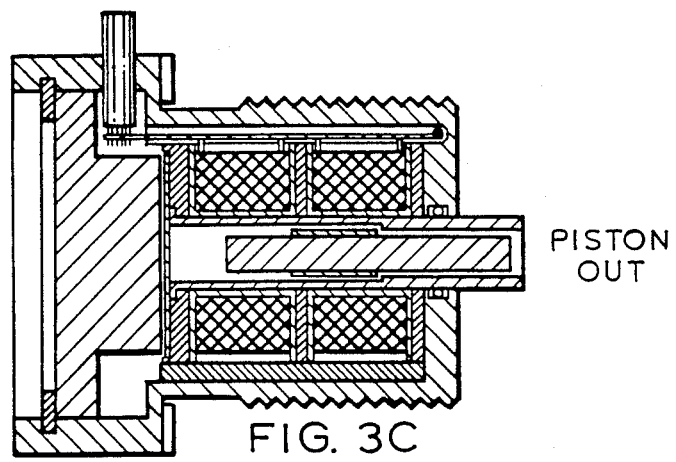
FIG. 3C — PISTON OUT

VISCOMETER

BACKGROUND OF THE INVENTION

The present invention is directed to viscometers.

U.S. Pat. No. 4,627,272 to Wright describes a viscometer in which a bob containing ferromagnetic material is disposed inside an elongated chamber that contains the fluid whose viscosity is to be measured. A pair of coils is disposed around the chamber and spaced longitudinally of it so as to enable the coils to draw the bob alternately in opposite directions. The Wright viscometer determines viscosity by measuring the time required to drive the bob through the fluid from one end of the path to the other.

As is stated in that patent, it is preferable that the bob be of substantially neutral buoyancy. The advantage of neutral buoyancy is that it makes the viscometer insensitive to vibration and to the orientation of the viscometer with respect to gravity.

But exact neutral buoyancy cannot always be achieved. The density of the fluid whose viscosity is to be measured sometimes varies. Moreover, the design constraints imposed by certain applications may make it more desirable that the mass of the bob be very low, and the result may be that the bob has significant positive buoyancy. For these reasons, the orientation of the viscometer can affect the accuracy of its measurement. Furthermore, the viscometer may be placed in a flowing fluid, and the orientation of the viscometer with respect to the flow direction can affect the measurement in those arrangements in which the bob is exposed to the flow.

A distinctive feature of the Wright viscometer is the manner in which it monitors bob position. Specifically, the bob includes ferromagnetic material and is positioned with respect to two coils so that its movement changes the mutual inductance between them. The viscometer circuitry then senses the electromotive force that alternating current in one coil induces in the other coil, and the bob is inferred to have reached a predetermined point in its travel when the magnitude of the induced AC signal falls to a predetermined fraction of its peak value for the current bob stroke.

The circuit for achieving this result includes a peak detector, which holds as its output the peak induced voltage for the current bob stroke. A comparator compares a predetermined percentage, say 90%, of this peak voltage with the instantaneous induced voltage. So long as the coil output has not fallen to 90% of its peak value, therefore, the output of the comparator is a square wave. The viscometer circuitry infers that the bob has reached the predetermined position when the square wave stops.

A determination that the square wave has stopped is made by a retriggerable monostable multivibrator, which is triggered repeatedly by the leading edges of the square wave. The monostable multivibrator remains triggered—i.e., in its unstable state—until the square wave stops, at which point the triggering stops and the monostable multivibrator resumes its stable state after its characteristic period has been completed. Resumption of the stable state is the indication that the bob has reached the predetermined position.

The period of the monostable multivibrator must be at least as great as the period of the AC signal induced in the coil; otherwise, the monostable multivibrator would resume its stable state before the square wave stopped. In practice, moreover, it is desirable for the period of the monostable multivibrator to be several times the period of the AC signal, because such a period length increases the immunity of the system to noise that might cause individual square-wave pulses to be missed. As a consequence, the monostable multivibrator imposes a certain delay in the system: the monostable multivibrator output does not resume its stable state until a fixed period of time after the square wave has stopped and thus after the bob has reached the predetermined position. The delay of the monostable multivibrator, though necessary, is thus a source of some inaccuracy.

Of course, the inaccuracy as a fraction of the total measurement can be reduced by increasing the length of bob travel, and thus the stroke duration, or by decreasing the period of the monostable multivibrator. But the period of the monostable multivibrator can be reduced only to the period of the AC signal, which noise considerations often require to be relatively long, and it is not always practical to increase the length of the bob stroke. Therefore, the monostable multivibrator used to indicate the presence or absence of the square wave is a source of inaccuracy.

An object of one aspect of the present invention is to reduce the flow- and gravity-induced inaccuracies that result from variations in viscometer orientation.

An object of another aspect of the present invention to reduce the inaccuracy caused by the monostable multivibrator without increasing stroke lengths or the frequency of the coil signal.

Another object of the invention is to measure fluid viscosity effectively.

SUMMARY OF THE INVENTION

The foregoing and related objects are achieved in a viscometer similar to that of the type described in the Wright '272 patent. Specifically, a bob is constrained by some guide, such as a cylinder that defines a fluid-containing chamber, to move in a path through a fluid whose viscosity is to be measured. The bob is driven back and forth along the path and sensing circuitry monitors the position of the bob. According to one aspect of the present invention, timing circuitry measures not just the duration of bob travel in one direction but the total duration of its travel in both directions. By basing the viscosity determination on total time, the effect of orientation variations can be greatly reduced.

Another aspect of the invention is applicable to viscometers that detect bob position by monitoring the mutual inductance between drive coils whose mutual inductance is affected by the position of the bob, which contains ferromagnetic material. The position-sensing circuit in such a viscometer generates a comparison signal that represents the comparison between (1) the instantaneous voltage induced in the undriven coil, and (2) a predetermined fraction of the peak value that the induced voltage achieved during the current bob stroke. The comparison signal is a square wave during the early part of the stroke, and the square wave stops when the bob reaches a reference point, at which the mutual inductance has fallen to a predetermined fraction of its peak value. To detect the fact that the square wave has stopped, the comparison signal is applied to a retriggerable monostable multivibrator whose period is greater than that of the induced voltage. The retriggerable monostable multivibrator thus remains in its unstable state until the square wave stops. It is the resumption of the stable state that causes the time measurement to stop and the coil driving to be reversed.

According to this aspect of the invention, the use of a second monostable multivibrator, this one having a period twice that of the first, significantly reduces the inaccuracy caused by the unavoidable delay of the monostable multivibrator. The second monostable multivibrator is triggered when the first resumes its stable state, and the time measurement does not resume until the second monostable multivibrator resumes its stable state.

Awaiting the stable state of the second monostable multivibrator before resuming time measurement compensates for the delay of the first monostable multivibrator. Specifically, in half of the time-out period of the second monostable multivibrator, the bob retraces that part of the travel that it performed during the delay of the first monostable multivibrator, so it has reached approximately the point in its travel at which the delay of the first monostable multivibrator began. The rest of the delay of the second monostable multivibrator occurs during the part of the travel that begins at the predetermined bob position, and this delay in beginning time measurement makes up for the extra time measurement that will occur at the previous stroke during the delay o the first monostable multivibrator. Thus, the inaccuracy resulting from monostable-multivibrator delay is reduced without increasing the frequency of the drive signal and without lengthening the distance of bob travel.

BRIEF DESCRIPTION OF THE DRAWINGS

These and further features and advantages of the present invention are described in connection with the accompanying drawings, in which:

FIGS. 3A, 3B, and 3C are cross-sectional views of the viscometer of FIG. 1 with the bob in different positions;

DETAILED DESCRIPTION OF ILLUSTRATIVE EMBODIMENTS

Figure 1:
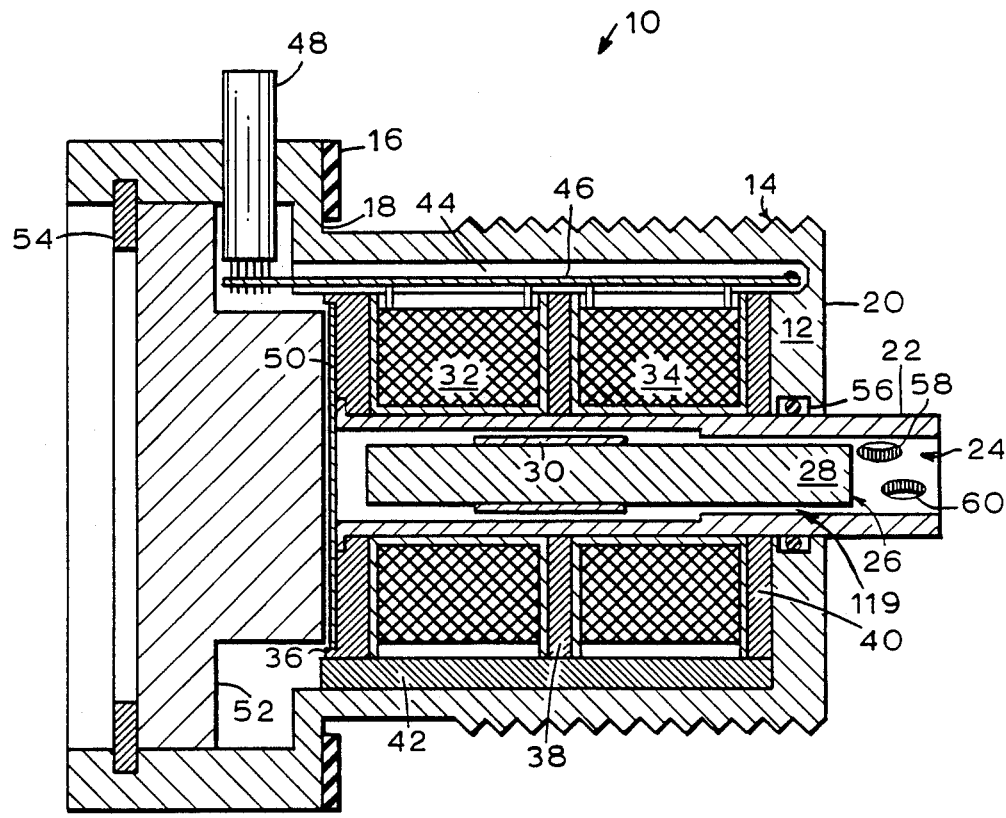
FIG. 1 is a cross-sectional view of the mechanical part of a viscometer that employs the teaching of the present invention.

FIG. 1 depicts in cross section the mechanical part 10 of a viscometer that embodies the teachings of the present invention. It includes a generally cylindrical shell 12 provided circumferentially with screw threads 14 intended to mate with corresponding threads in the wall of a pipe carrying the fluid whose viscosity is to be measured. When the viscometer 10 is screwed tightly into the pipe, an annular gasket 16 provides a seal between a shoulder 18 on the shell and the outside surface of the pipe.

The shell 12 includes an end wall 20 having a central opening through which a chamber-defining cylinder 22 protrudes. Disposed inside a chamber 24 formed by the cylinder 22 is a bob 26 for which the cylinder 22 serves as a guide. The bob includes a piston 28 preferably made of a material of high buoyancy. For most practical low-density materials, the magnetic permeability is low. To make the bob respond magnetically, the piston 28 is surrounded by a ring 30 made of a material whose magnetic permeability is relatively high, such as one of the 400 series (i.e., predominantly martensitic) stainless steels. Two coils 32 and 34 are disposed about, and spaced along, the chamber-forming cylinder 22. They are so disposed that they set up magnetic fields inside the chamber 24 when they are driven with electrical current. By driving coils 32 and 34 alternately, it is possible to cause the bob 26 to reciprocate in the chamber 24.

The ring 30 of high-permeability material affects the mutual inductance between coils 32 and 34, so bob position can be monitored by sensing this mutual inductance. Since the time required for a bob stroke depends on the viscosity of the fluid in chamber 24, the viscosity of that fluid can ultimately be inferred from mutual-inductance observations. In accordance with the present invention, the viscosity is determined not from the duration of travel in one direction only but rather from the total of the durations for both directions. With a proper choice of parameters, this reduces the effects of orientation on the viscosity measurement.

Specifically, the time required for a bob stroke from a point A on the left to a point B on the right under a constant magnetic force if inertial are non-Newtonian viscous effects are negligible is:

$$T_{ATB} = DV/kM \; (1/[1-(S\sin A)/M]),$$

where
$T_{ATB}$ = travel time from point A to point B;
D = distance from point A to point B;
M = magnetic force;
S = bob weight minus bob buoyant force, i.e., submerged weight; and
A = the angle that the bob path forms with the horizontal.

The time $T_{BTA}$ required for travel in the other direction is given by the following equation:

$$T_{BTA} = (DV/kM)(1/[1+(S\sin A)/M]).$$

Therefore, the sum T of the travel times in both directions is $$T = T_{ATB} + T_{BTA} = (DV/kM)\{2/[1-(S^2 \sin^2 A)/M^2]\}.$$

Inspection of these relationships reveals that measurement of the total of the durations in both directions reduces orientation-related inaccuracies whenever the magnetic force M on the bob exceeds the buoyant-force component S sin A in the direction of the bob path. Moreover, the ratio (S/M)sin A of two-stroke inaccuracy to one-stroke inaccuracy decreases with the ratio of the magnetic force to the in-path buoyant-force component.

To illustrate this effect, we consider two examples, one in which the ratio of submerged weight to magnetic force is 0.1 and the other in which the ratio is 0.5. In the former case, the error in viscosity measurement at a thirty-degree inclination from horizontal is five percent for a one-way measurement but only 0.25 percent for a two-way measurement. This is a twenty-fold improvement in orientation insensitivity. For S/M=0.5, the benefits are less but still very substantial; the error at thirty degrees is 25% for a one-way measurement but 5.9% for a two-way measurement.

The magnetic circuits of the coils 32 and 34 include generally annular disks 36, 38, and 40 disposed between and at the outer ends of coils 32 and 34. The disks 36, 38, and 40 are disposed inside a generally cylindrical ferromagnetic collar 42 contained in the shell 12. Although the collar 42 is generally cylindrical, it forms a longitudinal slot 44 in which a printed-circuit board 46 makes the connections between coils 32 and 34 and an electrical cable 48. The cable 48 leads to circuitry that will be described later in connection with FIG. 2.

The rear end of the chamber 24 is sealed by a resilient seal 50. A plug 52 applies pressure to the seal 50 and is held in place by a retaining ring 54 received in an annular recess in the shell 12. Seal 50 prevents fluid from reaching the coils by way of the opening in wall 20 through which the cylinder 22 protrudes, and an O-ring seal 56 is provided between the cylinder 22 and the surface that defines the central opening in wall 20. Alternatively, the seal could be provided by a weldment in place of the O-ring.

As the bob 26 reciprocates, it tends to refresh the contents of the chamber 24. Specifically, as it moves to the left, i.e., into the chamber, it tends to drive fluid to the right, i.e., into the pipe. In traveling back to the right, it tends to draw fluid back into the chamber 24. The viscometer would ordinarily be mounted so that the longitudinal direction of the bob 26 is transverse to the direction of flow through the pipe. The bob 26 is made long enough so that, in its rightmost position, it extends beyond the wall 20. If the cylinder 22 did not extend beyond the wall, therefore, the bob 26 would be positioned in the fluid flow, and this would tend to aid the refreshment process. In order to protect the bob 26, however, the cylinder 22 does extend beyond the wall 20, but the action of the flow in aiding the refreshment process is retained by the position of flow holes 58 and 60 in the cylinder 22.

FIG. 2 depicts the circuitry to which cable 48 of FIG. 1 connects. The circuitry includes a drive circuit 62 for alternately driving coils 32 and 34. The drive circuit 62 responds to an ATB signal, generated by direction-selection circuitry 64, which indicates the direction in which the drive circuit 64 is to drive the bob 26. The direction-selection circuitry 64, in turn, responds to detection circuitry 66, which monitors the mutual inductance between the coils 32 and 34 so as to determine when the bob 26 has reached either end of its travel. The output of the detection circuitry 66 is also employed by a time-measurement circuit 68, which generates an output representing the round-trip travel time of the bob 26.

The drive circuitry 62 includes a clock 70 whose output is a square wave having a DC level. A low-pass filter 72 removes the higher-frequency components from the square wave and so produces an output comprising a DC level with an approximately sinusoidal AC component superimposed. The purpose of the DC component is to provide the main drive current for the coils 32 and 34, while the purpose of the AC component is to cause current flowing in one coil to induce an electromotive force in the other so that the mutual inductance between the coils 32 and 34 can be monitored.

A switch 74 responds to the ATB signal to select the coil to which the switch 74 is to forward the output of the filter 72. The switch 74 forwards its output to one or the other of two current drivers 76 and 78, which drive coils 32 and 34, respectively. The drivers 76 and 78 are high-output-impedance circuits that produce currents whose magnitudes are determined by the voltages at their input ports and are not greatly affected by impedance changes in the coils 32 and 34. The ATB signal switches between high and low levels, and the coils 32 and 34 are alternately driven as a result; when coil 32 is being driven, coil 34 is not, and vice versa.

The complement of the ATB signal is a BTA signal, which the direction-selection circuitry 64 applies to a switch 80 in the detection circuitry 66. The two inputs of switch 80 are the voltages across coils 32 and 34, and switch 80 selects one of these inputs, in accordance with the BTA signal, to apply the output of the non-driven coil to a filter 82. Filter 82 is a band-pass filter that increases the signal-to-noise ratio of the system by passing only the fixed fundamental frequency of the clock 70. Filter 82 feeds its output to the remainder of the detection circuitry 66. The purpose of this circuitry is to determine when the bob 26 has reached a predetermined point in each direction of travel.

When the bob 26 begins its left-to-right stroke, it starts in a position illustrated in FIG. 3A, in which most of the ferromagnetic ring 30 is disposed between ferromagnetic disks 36 and 38, and the mutual inductance between coils 32 and 34 is thus relatively low. As it moves to the right from this position, the ferromagnetic ring 30 increases the magnetic coupling between the coils until the mutual inductance reaches a maximum when the bob 26 is in the position depicted in FIG. 3B. Continued travel toward the rightmost position depicted in FIG. 3C, however, reduces the mutual inductance again. The detection circuitry of FIG. 2 detects the point at which the bob 26 has reached a predetermined position toward the end of its rightward travel by determining when the mutual inductance has fallen to a predetermined percentage of the peak mutual inductance. It does this by determining when the amplitude of the AC signal on the non-driven coil falls to a predetermined percentage of its peak amplitude.

Specifically, the filter 82 applies its output to a peak detector 84, which retains as its output the highest instantaneous voltage that it has received from filter 82 since the time, at the beginning of the stroke, at which the peak detector 84 was last reset. This peak voltage is divided by a voltage divider 86 to a value that is, say, 90% of the peak output of peak detector 84. A comparator 88 subtracts this 90-per-cent-peak signal from the filter output, and the comparator 88 therefore produces a square wave so long as the peak of the filter output remains at least 90% of the highest peak that it previously attained during the current stroke. That is, the comparator output remains a square wave as the mutual inductance increases with rightward travel, and it continues until the mutual inductance falls to a 90% level. At that point, the square wave ceases, indicating that the predetermined position has been reached.

A gate 90 forwards the comparator output to a retriggerable monostable multivibrator 92 whose purpose is to generate a high output so long as the square wave is present; i.e., its output must stay high between triggerings by the low-to-high transitions of the comparator output, but it must eventually go low when the square wave ceases. Accordingly, its period is greater than the clock period and thus greater than the period of the square-wave output of the comparator 88.

In practice, it is preferable for time-out period of monostable multivibrator 92 to be at least several clock periods, because this makes the detection circuitry relatively immune to noise that might cause a pulse to be missing from the output of comparator 88. The absence of such a pulse would otherwise cause the direction to be switched prematurely.

So long as the square wave is present, the monostable multivibrator 92 never returns to its stable state. But when the bob 26 reaches the predetermined position and the square wave ceases, triggering of the monostable multivibrator 92 stops, and its output accordingly goes low after its characteristic delay. As will be explained below, this low-going edge stops the timing of the current bob stroke. It also triggers a second monostable multivibrator 94, whose lower output in FIG. 2B goes from a high state to a low state. This high-to-low transition causes an immediate change in the states of switches 74 and 80, thereby causing the coil selection for driving and sensing to be reversed, as will be described presently. Bob travel thus reverses immediately after timing stops.

Monostable multivibrator 94 has a period twice that of monostable multivibrator 92. For that length of time, the lower output of monostable multivibrator 94 disables gate 90 to compensate for the delay of monostable multivibrator 92, as will be explained below. The low-to-high transition of the complementary, upper output of monostable multivibrator 94 resets the peak detector so that its output goes to zero and can be used on the return stroke to detect the other 90% position.

To time a bob stroke, a digital divider 96 in the time-measurement circuit 68 receives the output of the clock 70 and produces a square wave having a period equal to an integral number of clock periods. An AND gate 98 forwards the divider output to a counter 100 so long as the output of monostable multivibrator 92 is high. That is, the AND gate 98 forwards the count pulses as the bob 26 travels to the 90% point, and it continues forwarding pulses after the bob passes the 90% point until the time at which monostable multivibrator 92, which the comparator output no longer triggers after the 90% point is reached, times out and generates a low output. This output disables gate 98, and counter 100 stops receiving pulses.

As will be explained in more detail below in connection with FIG. 4, this means that, although the viscometer works on the principle of measuring the travel time for a known distance, the part of each bob stroke that the time-measurement circuit 64 times in each half of a bob round trip is not, strictly speaking, a fixed distance; the time-measurement circuit 64 measures the time required for the bob to get to the point that it reaches when it has traveled beyond the 90% point for one period of monostable multivibrator 92. As will become apparent, however, this departure from a fixed distance can be made arbitrarily small to meet the required accuracy, so the distance is, for all practical purposes, known.

As was previously mentioned, the circuit of FIG. 2 measures the sum of the times taken by two successive bob strokes. Specifically, it first measures the time of the A-to-B stroke and then adds the time of the B-to-A stroke. At the end of the B-to-A stroke, the output of counter 100 represents the total of the times for two successive strokes and is thus an indication of the fluid's viscosity. In the illustrated embodiment, this indication is recorded when, at the end of the B-to-A stroke, the ATB signal goes high and thereby triggers a monostable multivibrator 102, whose output causes a digital-to-analog converter 104 to latch the counter output. The resultant analog voltage can be used for various process purposes, or it might be used simply to drive a meter 106, which displays the viscosity measurement.

It can be appreciated that the output of the digital-to-analog converter 104, and thus the reading on meter 106, for a given viscosity depend on the setting of programmable divider 96. Accordingly, divider 96 acts as a gain selector.

When monostable multivibrator 102 times out, i.e., after the digital-to-analog counter has latched in the contents of counter 100, its trailing edge triggers another monostable multivibrator 108, whose resultant output resets counter 100 so that it can begin a new count. The direction-selection circuitry 64 receives the lower output of monostable multivibrator 94 at an input port of a NAND gate 110, whose other input is the normally high output of a time-out counter 112. Accordingly, the output of NAND gate 110 is usually low, but it goes high on the falling leading edge of the output of monostable multivibrator 92, thereby clocking a J-K flip-flop 114, whose J and K input ports are tied to a logic 1 so that the flip-flop 114 toggles on each clock pulse that it receives. The complementary outputs of the direction-selection flip-flop 114 are the ATB and BTA signals previously described; i.e., the state of flip-flop 114 determines which coil is driven and which coil is sensed.

Time-out counter 112 is set to produce a pulse after it has reached a predetermined count. The predetermined count represents a time interval that is typically 20% higher than the highest expected bob-stroke duration, but counter 112 is reset by monostable 94 when the bob reaches its point. Consequently, time-out counter 112 is usually reset before its output has had a chance to go low. The direction-selection flip-flop 114 thus is ordinarily toggled by the detection circuitry and not by the time-out counter 112. The time-out counter 112 is necessary to produce a toggle pulse on start-up, however, and it also produces toggle pulses to enable the system to recover if the detection circuitry 66 fails for some reason to detect the passage of the bob 26 through the detection point.

Figure 2A:
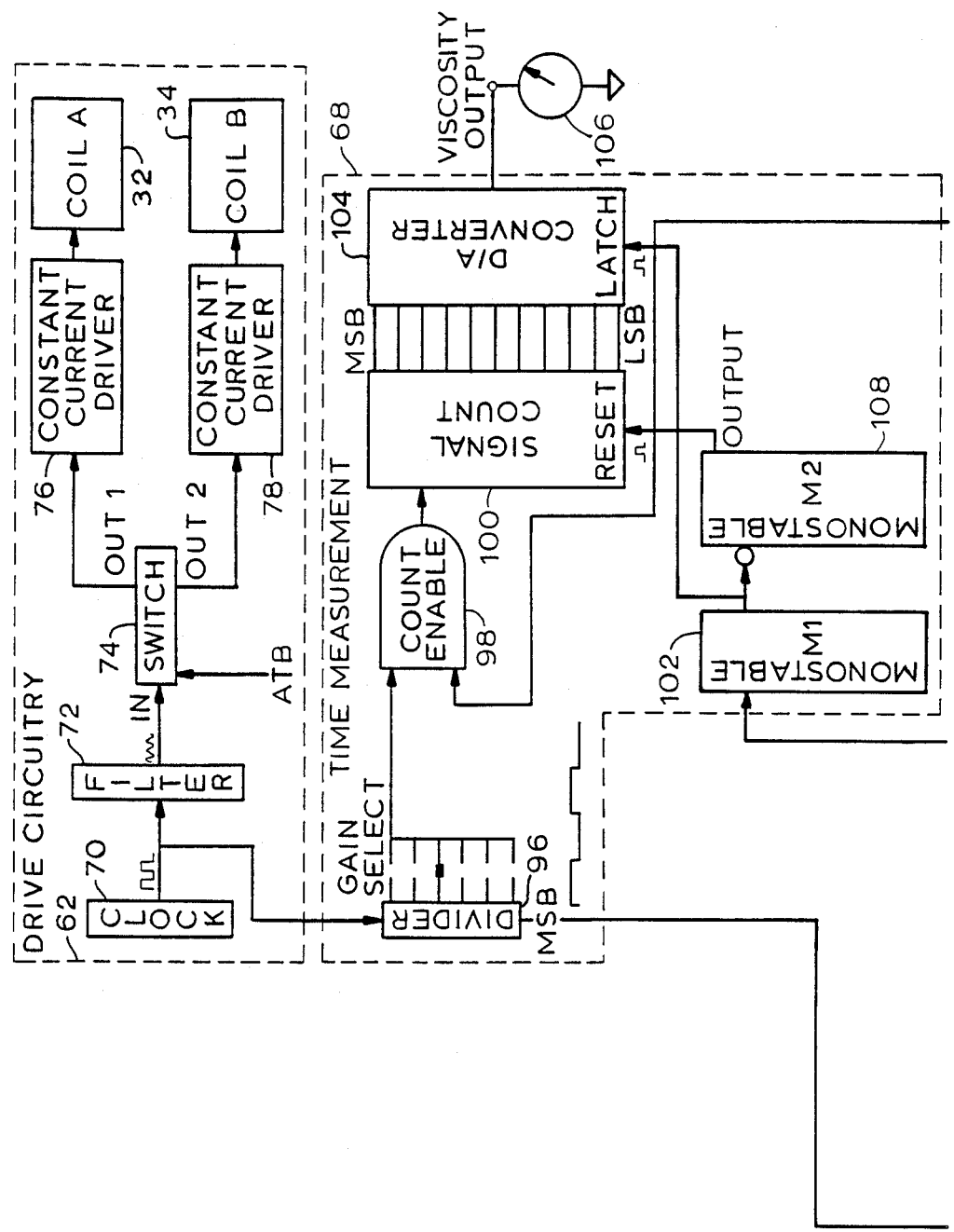
FIG. 2A and 2B depict a block diagram of the circuitry for driving the viscometer coils, sensing bob position, and measuring travel time so as to generate a viscosity indication.
Figure 2B:
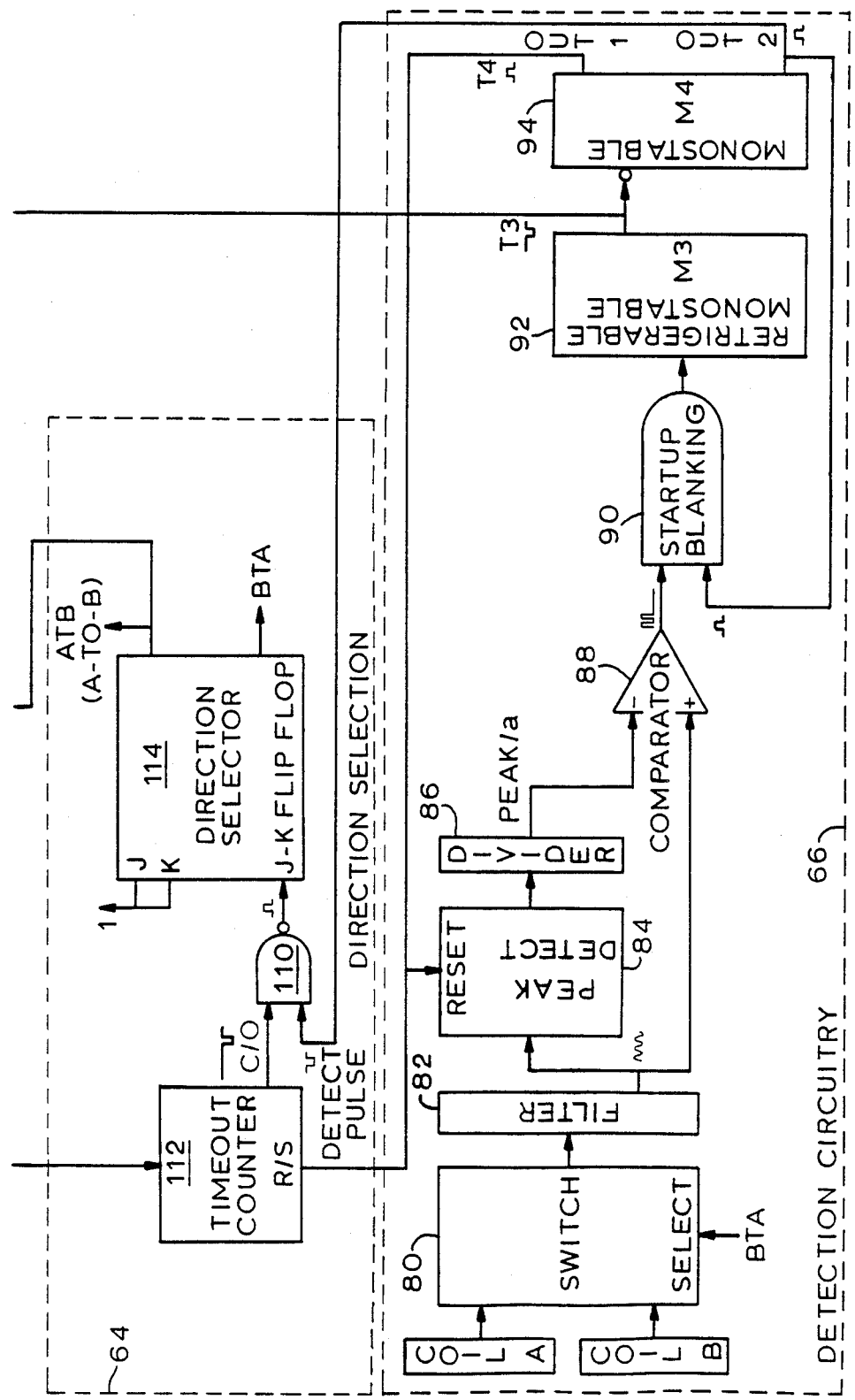
Figure 4A:
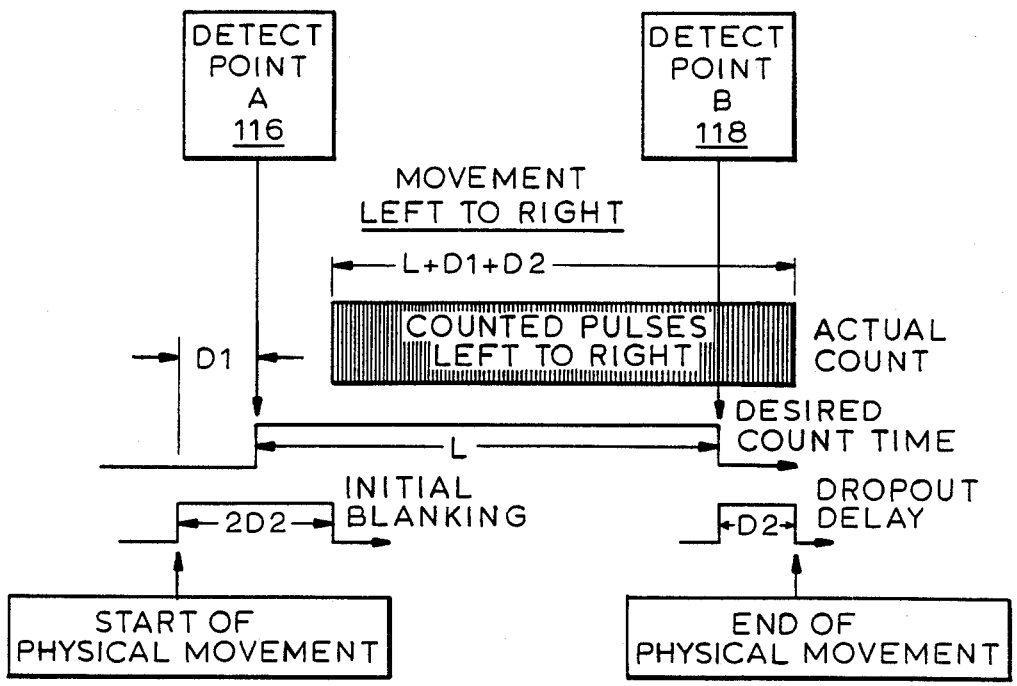
FIGS. 4A and 4B are diagrams illustrating bob travel and the part of that travel during which the circuitry measures time.

Operation of the circuitry of FIGS. 2A and 2B will be described in connection with the diagram of FIGS. 4A and 4B, which represent the motion of the bob 26. Detect points 116 and 118 represent the two points in the travel of bob 26 at which the mutual inductance falls below 90% of its peak value and the square-wave output of the comparator 88 therefore ceases. The distance between these two points will be assumed to be L, and the viscometer operates, in principle, by measuring the time required to traverse the distance in two directions. Therefore, the teachings of the present invention could be practiced in an embodiment in which the time measurement in counter 100 is simply stopped when the comparator-88 square wave stops. For purposes that will become apparent as the description proceeds, however, the illustrated embodiment does not stop the counting immediately when the bob 26 reaches a detect point 116 or 118.

Specifically, when the bob passes to the left (in the B-to-A direction) through 90% point 116, the square wave produced by comparator 88 stops, so triggering of monostable multivibrator 92 does, too. The period of monostable multivibrator 92 then passes, after which its output goes low and triggers monostable multivibrator 94, thereby causing the coil drive to switch, as was described above. At the same time, AND gate 98 is disabled, so counter 100 stops receiving pulses and is no longer being incremented. Also, since the B-to-A stroke has just ended, the output of counter 100 is latched into the digital-to-analog converter 104, and counter 100 is then reset after the time-out period of monostable multivibrator 106. In the time required for monostable multivibrator 92 to time out and thus stop counter 100, the bob 26 has passed beyond point 116 by a distance $D_1$. Therefore, the bob begins its A-to-B (left-to-right) stroke from a point $D_1$ beyond point 116, as FIG. 4A indicates.

The time measurement does not begin at that point, however. As was stated above, the timing out of monostable multivibrator 92 triggers monostable multivibrator 94, whose lower output thereby goes low and disables gate 90 at the same time as the upper output of monostable multivibrator 94 resets the peak detector 84 and thus causes the square-wave output of comparator 88 to resume. As a result, the pulses from comparator 88 do not initially trigger monostable multivibrator 92, and its output remains low, keeping AND gate 98 disabled and thus preventing further count pulses from reaching counter 110.

The period of monostable multivibrator 94 is twice that of monostable multivibrator 92, so the duration of the time during which the lower output of monostable multivibrator 94 disables gate 90—and ultimately prevents pulses from reaching the (now-reset) counter 100—is twice that during which the bob traveled by distance $D_1$. In this length of time, the bob travels a distance $2D_2$ back to the right, as FIG. 4A indicates, and counter 100 receives no count pulses during that part of bob travel. Accordingly, time measurement does not begin until the bob has reached a distance $2D_2-D_1$ to the right of point 116.

Counting then begins and continues until the bob reaches a point $D_2$ to the right of point 118, at which time monostable multivibrator 92 again times out and stops counter 100. This time, however, the ATB signal goes low rather than high, so it does not trigger monostable multivibrator 102, and the digital-to-analog converter 104 and counter 100 are not latched and reset, respectively. Instead, counter 100 merely holds its count, which the digital-to-analog converter 104 does not latch. At this point, therefore, counter 100 contains a count that represents the time that has been required for the bob to travel a distance equal to $L+D_2-(2D_2-D_1)=L+D_1-D_2$, as FIG. 4A indicates. If the bob is strictly horizontal, $D_1=D_2$, so this value reduces simply to L.

Figure 4B:
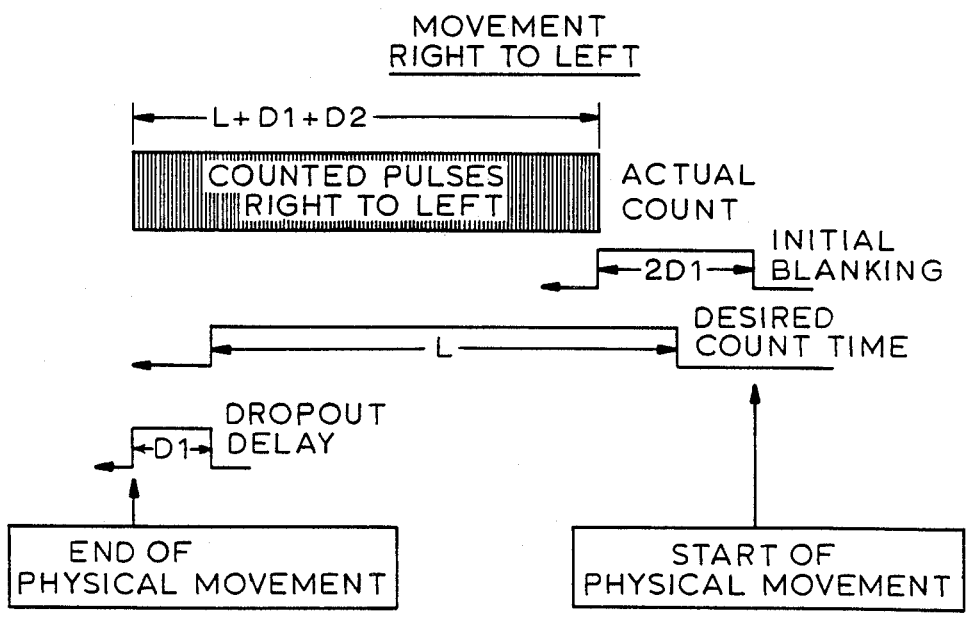

FIG. 4B depicts the B-to-A stroke and indicates that the count resumes when the bob reaches a point $2D_1-D_2$ to the left of detect point 118, and it continues until the bob reaches a point $D_1$ to the left of detect point 116. In resuming the count, the counter 110 adds up an additional time equal to the time required for the bob to travel a distance $L+D_1-(2D_1-D_2)=L-D_1+D_2$. Thus, the total distance measured is 2L. If the bob travel has been totally horizontal, a bob travel of L in one direction has been added to a bob travel L in the other direction, which is exactly what is desired. If the bob travel is not strictly horizontal, the distances that the circuitry has measured differ by $2(D_1-D_2)$, but this can be made to be a distance very small in comparison with L, so the accuracy penalty exacted by the functions of monostable multivibrators 92 and 94 can be kept small.

Figure 5:
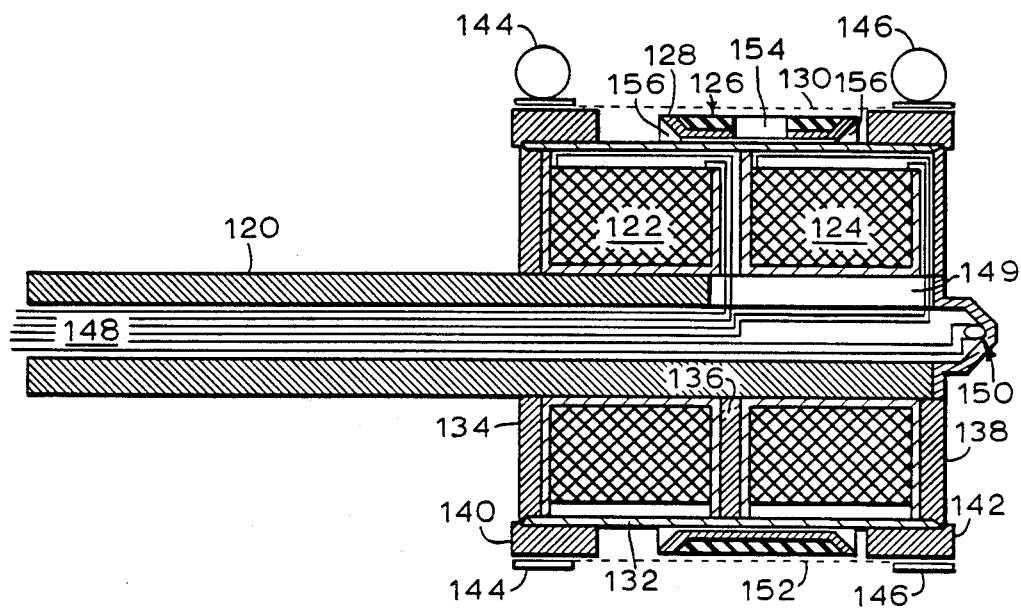
FIG. 5 is a cross-sectional view of the mechanical part of an alternate embodiment of the present invention.

Inspection of the fit between the bob and the chamber walls in FIG. 1 reveals that relatively low bob velocities result in high fluid velocities in the narrow annular regions surrounding the ferromagnetic ring 30 and around that part of the piston 28 in the narrower, neck region 119 of the chamber 24. This enables the design depicted in FIG. 1 to measure very low viscosities. For fluids that have relatively high viscosities, however, the arrangement of FIG. 1 is somewhat less desirable, and an alternative arrangement, depicted in FIG. 5, is preferred.

In this arrangement, the outer shell 12 of FIG. 1 is replaced with an internal tube 120 about which two coils 122 and 124 are wound. These coils correspond to coils 32 and 34 of FIG. 1. Replacing the internal bob 26 is an external movable cylindrical shuttle 126, which includes a ferromagnetic main member 128 and a sleeve 130 disposed about the main member and made of positive-buoyancy material. In many applications, it is desirable for the relative sizes of the two components of the shuttle 126 to give it approximately a neutral buoyancy, although, as was mentioned above, other considerations may necessitate other densities.

The shuttle 126 is disposed about a low-permeability sleeve 132, which serves as a shuttle guide. The sleeve 132 is mounted to the tube 120 by means of disks 134, 136, and 138, which correspond to similar disks 36, 38, and 40 of FIG. 1. The tube 120 is preferably made of a high-magnetic-permeability material so as to increase the resultant flux density in the region of the shuttle 126. For support of the filtering screen and provision of a physical limit to shuttle motion, collars 140 and 142 are disposed about sleeve 132 just beyond the ends of the intended shuttle travel. The collars may be held in place by respective clamps 144 and 146. Leads in a cable 148 corresponding to cable 48 of FIG. 1 reach the coils 122 and 124 through the interior of the tube 120 and a longitudinal slot 149 in the tube.

It may be desirable to record the ambient temperature for temperature compensation and other purposes. If so, the cable 148 may include leads that connect to a thermocouple or other temperature-indicating device 150 disposed at the end of the tube 120.

In the illustrated embodiment, a cylindrical screen 152 is disposed around the collars 140 and 142 and outside the shuttle 126 to protect the shuttle 126 from fouling. Reciprocation of the shuttle 126 causes the screen 152 to be purged as the shuttle drives fluid out of its path and through the screen 152.

To enhance the flushing action, one or more holes or slots 154 can be drilled in the shuttle 126. To enhance flushing further as well as to contribute to fluid replacement in the annulus between the shuttle 126 and sleeve 132, a bevel 156 or angle can be cut on one or more shuttle faces to force fluid into the annulus when the shuttle moves.

In the embodiment of FIG. 5, the two-stroke viscosity measurement has an additional advantage. Since the viscometer may be disposed in a flowing fluid and the fluid flow may have a component parallel to the shuttle axis, the flow can affect the shuttle stroke time and thus the accuracy of the viscosity measurement. By making a two-stroke measurement, however, the measurement inaccuracy can be reduced.

Although only two embodiments of the invention have been described, it is apparent that a wide variety of embodiments can be employed that follow the teachings of the present invention. For instance, the broader teachings can be used in viscometers in which bob travel is detected without resort to initial-inductance sensing or electromagnetic bob driving. The present invention thus constitutes a significant advance in the art.

What is claimed as new and desired to be secured by Letters Patent of the United States is:

1. A viscometer comprising:
   A. a bob;
   B. guide means for guiding the bob along a bob path through a fluid whose viscosity is to be measured;
   C. bob-driving means for driving the bob alternately in opposite directions along the bob path with a predetermined force;
   D. sensing and measuring means for monitoring bob position, measuring the average of the travel times required for the bob to travel known distances in both directions along the bob path, generating an indication of the measured time, and thereby indicating the viscosity of the fluid whose viscosity is to be measured.

2. A viscometer as defined in claim 1 wherein:
   A. the bob includes ferromagnetic material; and
   B. the bob-driving means includes (1) first and second coils disposed adjacent the path for producing, when the coils conduct current, magnetic fields in the path that drive the bob in opposite directions and (2) a current-driver circuit for alternately driving current through the first and second coils.

3. A viscometer as defined in claim 2 wherein:
   A. the first and second coils are so oriented that their mutual inductance is a function of bob position; and
   B. the sensing and measuring means comprises means for monitoring the mutual inductance of the coils and measuring the travel time by measuring time intervals defined by the times at which the monitored inductance reaches points in its position function that correspond to predetermined bob positions.

4. A viscometer as defined in claim 1 wherein:
   A. the bob includes ferromagnetic material;
   B. the viscometer includes first and second coils disposed adjacent the path and so oriented that their mutual inductance is a function of bob position; and
   C. the sensing and measuring means comprises means for monitoring the mutual inductance of the coils and for measuring the travel time by measuring a time interval defined by the times at which the monitored inductance reaches points in its position function that correspond to predetermined bob positions.

5. A viscometer as defined in claim 1 wherein:
   A. the bob includes ferromagnetic material;
   B. the bob-driving means includes:
      i. first and second coils so disposed adjacent the path that their mutual inductance is a function of bob position and that, when the coils conduct current, they produce magnetic fields that tend to drive the bob in opposite directions along the path; and
      ii. a coil driver responsive to control signals applied thereto to select between the first and second coils, the coil driver being coupled to the coils to drive electric current through the selected coil, whereby the bob can be driven back and forth along the bob path in oppositely directed strokes;
   C. the sensing and measuring means includes:
      i. a position-sensing circuit coupled to the coils for generating a comparison signal representing the comparison of (a) the instantaneous voltage induced in the non-selected coil with (b) a predetermined fraction of the peak value achieved by the induced voltage during the current bob stroke, whereby the comparison signal comprises a square wave having first-and second-direction transitions so long as the induced voltage is an AC signal whose amplitude remains above the predetermined fraction of its peak amplitude;
      ii. a delay circuit comprising:
         a. a retriggerable first monostable multivibrator having a first period and being coupled for triggering by first-direction transitions of the comparison signal;
         b. a second monostable multivibrator having a second period greater than the first period and being coupled for triggering by transitions of the output of the first monostable multivibrator that represent resumption of the stable state of the first monostable multivibrator; and
      iii. timing circuitry responsive to the delay circuitry to measure time intervals that start when the second monostable multivibrator resumes its stable state and end when the first monostable multivibrator resumes its stable state, the timing circuitry generating an indication of the measured time and thus of the viscosity of the fluid whose viscosity is to be measured; and
   D. the bob-driving means further includes direction-control circuitry coupled to the coil driver for application of control signals thereto and responsive to resumption by the first monostable multivibrator of its stable state to apply to the coil driver control signals that switch the coil selection by the coil driver.

6. A viscometer as defined in claim 5 wherein:
   A. the viscometer includes a gate responsive to the state of the second monostable multivibrator and interposed between the position-sensing circuit and the first monostable multivibrator to prevent the first monostable multivibrator from being triggered by the comparison-signal transitions when the second monostable multivibrator is in its unstable state but to permit the first monostable multivibrator to be triggered by the comparison-signal transitions when the second monotable multivibrator is in its stable state; and
   B. the timing circuitry measures the time intervals during which the first monostable multivibrator is in its unstable state.

7. For measuring the viscosity of a fluid, a method comprising the steps of:
   A. providing a bob;
   B. driving the bob through the fluid alternately in opposite directions along a bob path with a predetermined force;
   C. taking a measurement of the average of the travel times required for the bob to travel known distances in both directions along the bob path; and
   D. generating an indication of the measured time and thereby of the viscosity of the fluid.

8. A viscometer comprising:

A. a bob including ferromagnetic material;
B. guide means for guiding the bob along a bob path through a fluid whose viscosity is to be measured;
C. first and second coils so disposed adjacent the path that their mutual inductance is a function of bob position and that, when the coils conduct current, they produce magnetic fields that tend to drive the bob in opposite directions along the path;
D. a coil driver responsive to control signal applied thereto to select between the first and second coils, the coil driver being coupled to the coils to drive electric current through the selected coil, whereby the bob can be driven back and forth along the bob path in oppositely directed strokes;
E. a position-sensing circuit coupled to the coils for generating a comparison signal representing the comparison of (1) the instantaneous voltage induced in the non-selected coil with (2) a predetermined fraction of the peak value achieved by the induced voltage during the current bob stroke, whereby the comparison signal comprises a square wave having first- and second-direction transitions so long as the induced voltage is an AC signal whose amplitude remains above the predetermined fraction of its peak amplitude;
F. a delay circuit comprising:
  i. a retriggerable first monostable multivibrator having a first period and being coupled for triggering by first-direction transitions of the comparison signal; and
  ii. a second monostable multivibrator having a second period greater than the first period and being coupled for triggering by transitions of the output of the first monostable multivibrator that represent resumption of the stable state of the first monostable multivibrator;
G. direction-control circuitry coupled to the coil driver for application of control signals thereto and responsive to resumption by the first monostable multivibrator of its stable state to apply to the coil driver control signals that switch the coil selection by the coil driver; and
H. timing circuitry responsive to the delay circuit to measure time intervals that start when the second monostable multivibrator resumes its stable state and end when the first monostable multivibrator resumes its stable state, the timing circuitry generating an indication of the measured time and thus of the viscosity of the fluid whose viscosity is to be measured.

9. A viscometer as defined in claim 8 wherein:
A. the viscometer includes a gate responsive to the state of the second monostable multivibrator and interposed between the position-sensing circuit and the first monostable multivibrator to prevent the first monostable multivibrator from being triggered by the comparison-signal transitions when the second monostable multivibrator is in its unstable state but to permit the first monostable multivibrator to be triggered by the comparison-signal transitions when the second monostable multivibrator is in its stable state; and
B. the timing circuitry measures the time intervals during which the first monostable multivibrator is in its unstable state.

10. A method of measuring viscosity comprising the steps of:
A. providing a bob that includes ferromagnetic material and is adapted to be driven back and forth along a bob path through a fluid whose viscosity is to be measured;
B. providing first and second coils so disposed adjacent the path that their mutual inductance is a function of the position of the bob along the path;
C. driving the bob back and forth in strokes along the bob path with a predetermined force;
D. causing an alternating current to flow in one of the coils while the bob is being driven;
E. sensing the voltage induced in the other coil and performing a comparison of (1) the instantaneous voltage induced in the non-selected coil with (2) a predetermined fraction of the peak value achieved by the induced voltage during the current bob stroke, whereby the comparison changes between two values so long as the induced voltage is an AC signal whose amplitude remains above the predetermined fraction of its peak amplitude;
F. changing the direction in which the bob is driven a first period of time after the comparison has changed to a given value and remained at that value in the interim, the first period being greater than the period of the AC signal;
G. measuring time intervals that begin a second period after direction changes and end at the subsequent direction changes, the second period being greater than the first period; and
H. generating an indication of the length of the measured time intervals and thus of the viscosity of the fluid whose viscosity is to be measured.

* * * * *